United States Patent [19]

Liu et al.

[11] Patent Number: 4,928,537
[45] Date of Patent: May 29, 1990

[54] SYSTEM FOR AIRBORNE PARTICLE MEASUREMENT IN A VACUUM

[75] Inventors: Benjamin Y. H. Liu, North Oaks, Minn.; Wladyslaw W. Szymanski, Vienna, Australia

[73] Assignee: Regents of the University of Minnesota, Minneapolis, Minn.

[21] Appl. No.: 280,483

[22] Filed: Dec. 6, 1988

[51] Int. Cl.⁵ .................. G01N 15/10; G01N 1/24; G06M 11/00

[52] U.S. Cl. .................. 73/863.86; 73/863.83; 73/864.33; 377/10

[58] Field of Search ........... 73/864.81, 864.83, 864.84, 73/864.85, 863.83, 863.87, 863.86, 28, 863.81, 864.33, 862.82, 863.85, 864.82, 864.86, 864.87; 377/10, 12; 324/71.4; 364/555; 250/222.2; 356/335–343

[56] References Cited

U.S. PATENT DOCUMENTS

| | | | |
|---|---|---|---|
| 3,554,038 | 1/1971 | Sweeney et al. | 73/863.83 |
| 3,892,549 | 7/1975 | Lyshkow | 73/864.81 X |
| 3,953,792 | 4/1978 | Wortman et al. | 377/10 X |
| 3,976,450 | 8/1976 | Marcote et al. | 73/864.81 X |
| 4,577,517 | 3/1986 | Knight | 73/864.81 |
| 4,607,526 | 8/1986 | Bachenheimer et al. | 73/864.81 X |
| 4,641,541 | 2/1987 | Sharp | 73/864.81 |
| 4,739,177 | 4/1988 | Borden | 356/338 X |
| 4,791,820 | 12/1988 | Lawrence et al. | 73/864.81 X |
| 4,792,199 | 12/1988 | Borden | 356/37 |
| 4,799,394 | 1/1989 | Barnett et al. | 73/864.81 |

FOREIGN PATENT DOCUMENTS 1124732 3/1962 Fed. Rep. of Germany ... 73/863.86

OTHER PUBLICATIONS

Microcontamination, Oct. 1987, "Monitoring Particles in Vacuum-Process Equipment", Peter G. Borden et al., pp. 30–34.

Primary Examiner—Tom Noland
Attorney, Agent, or Firm—Kinney & Lange

[57] ABSTRACT

A particle measurement apparatus for obtaining accurate information relating to airborne particles in a gas under vacuum from a process chamber including a sampling chamber which can be subjected to a very strong vacuum and used for obtaining a sample of the gas in the process chamber. The interior of the sampling chamber is first flushed with very clean purge gas, and subsequently opened to the process vacuum chamber which is to be sampled so that a sample of the atmosphere of gas from the process vacuum chamber is held in the sampling chamber. The sampling chamber is sealed from the process chamber and the sample is brought to atmospheric pressure by adding a particle-free purified gas. The sample is then flushed from the sampling chamber and passed through a particle counter. Calculations can then be made to determine the original particle concentration in the process vacuum chamber based on the measured particle concentration from the sample of the sampling chamber. By having a series of valves operated in a selected sequence, a very accurate measurement of particles down to as small as 0.01 microns can be measured, and the system can be used to measure particles in chambers under from about one atmosphere to approximately 0.001 atmosphere.

11 Claims, 2 Drawing Sheets

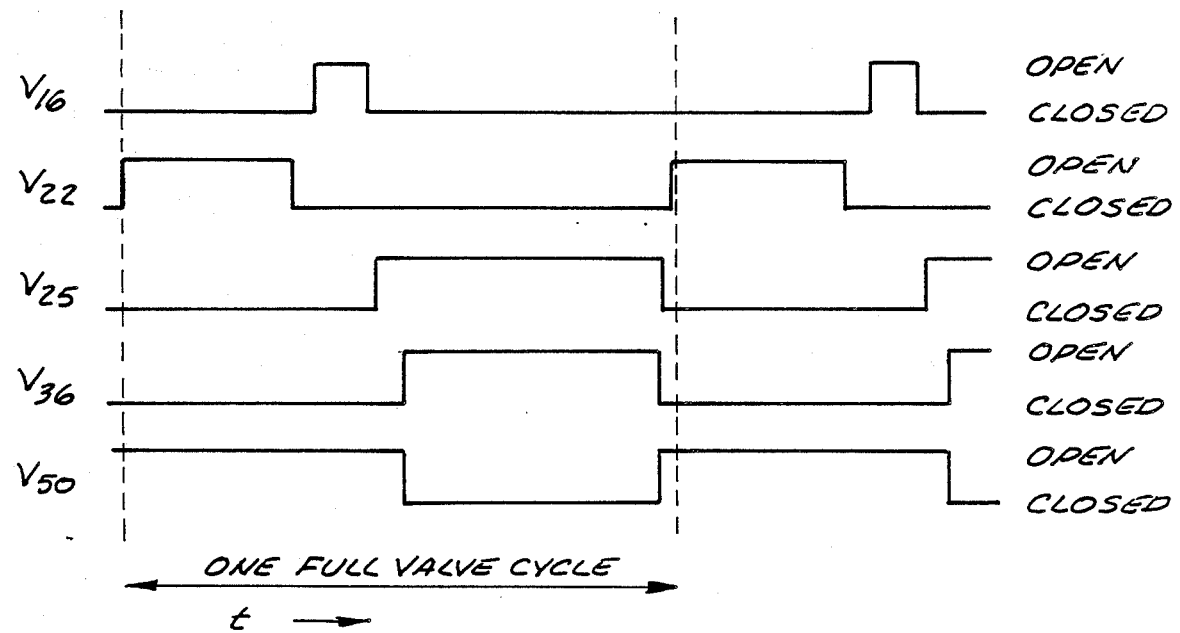

SYSTEM FOR AIRBORNE PARTICLE MEASUREMENT IN A VACUUM

BACKGROUND OF THE INVENTION

1. Field of the Invention

The present invention relates to a system for measuring airborne particles in a gas under vacuum, and a method for carrying out this measurement.

2. Description of the Prior Art

Many industrial processes, particularly those used in the microelectronic industry for fabricating integrated circuits are carried out in process chambers operated under conditions of reduced pressure. The processing not only is carried out in vacuum chambers, but must be done under extremely clean conditions because small particles suspended in a gaseous environment or atmosphere in the process chamber can deposit on the wafer or chip being processed, causing the product to degrade in performance. Sometimes the products are actually made non-functional by very small particles that are deposited during the process being carried out. This results in a loss of yield of the product, and considerable economic loss to the manufacturer.

The processes occur in large process vacuum chambers, and involve pumping down the gas for processing and venting the chamber at the completion of a process. This cycling of the process chamber gas may result in the generation of large quantities of airborne particles. At the present very little is known about particle generation in vacuum systems because there is a lack of suitable instrumentation for directly making particle concentration measurements in vacuums. It is known that some of the particles will deposit on walls of the vacuum system or chamber, and then will be dislodged during interchange of the vacuum atmosphere in a process cycle. Particles also can be produced by homogeneous and heterogeneous nucleation, followed by vapor condensation.

A recent development in the area of particle measurement in vacuums is a device called the PM-100 Particle Flux Monitor, manufactured by the High Yield Technology Company of Mountain View, California. This device has been described in an article by Borden et al., entitled "Monitoring Particles in Vacuum-Processing Equipment" *Microcontamination,* 5:30-34 (1987). The undersigned inventor also has been involved in an evaluation of this type of device, as set forth in an article that has been submitted for publication in *Aerosol Science Technology.*

Another way that particles have been measured in vacuum systems is to place a test surface (generally a wafer that is being processed) in the process vacuum chamber. Particles deposited on the surface of the wafer can be detected and measured by a light microscope or photographic methods. The lower size limit that can be measured by this method is about two microns. Another method or system involves scanning a wafer surface using a laser beam and measuring the scattered light caused by the particles with an optical detection system. The equipment for making the particle measurement is extremely expensive, and even the best equipment is limited to a lower particle size detection limit of about 0.2 microns. The equipment does not count particles in the actual vacuum environment, that is, while the particles are suspended in the gas or atmosphere, but is usable only after the particles have been deposited on a test wafer surface, and the wafer has been removed from the process vacuum chamber.

Thus, the present methods of measuring particles or aerosols in a vacuum do not provide measurements substantially in real time, or very close thereto. In real time measurements, the generation and decay of particles in the vacuum can be followed without disturbing the ongoing process in the vacuum, that is, without breaking the vacuum or disrupting the manufacturing process.

SUMMARY OF THE INVENTION

The present invention relates to improved instrumentation, and a method of use, for measuring concentration of particles by counting particles in a process vacuum chamber without disrupting the manufacturing process, and without breaking the vacuum in the process vacuum chamber, while at the same time providing substantially a real time count of the particles.

The instrument or apparatus comprises a sample chamber and a series of valves for controlling air flow, as well as a conventional particle analyzer. A gas or atmosphere sample is taken from the process vacuum chamber being monitored, and is kept pure, that is, only mixed or handled with other gases that are free of particles. After moving a gas sample from the process vacuum chamber to the sample chamber, the sample vacuum chamber is closed off from the main process vacuum chamber and is brought up to atmospheric pressure. The sample chamber is then flushed of the gas and particles in it, and the gas is passed through a conventional, highly accurate particle counting instrument that can count particles in the range of about 0.1 micron to 0.01 micron.

Any deposition of suspended particles onto surfaces, or regeneration of new particles in the gas sample from the process vacuum chamber is kept at a minimum because of the method of handling the gas sample.

The sample vacuum chamber is of suitable volume and is opened to the process vacuum chamber through a line and a controllable valve. A series of other valves are used, which are opened or closed in an appropriate sequence to cause a sample of gas to be taken from some suitable sampling point in the process vacuum chamber, and passed into the pre-evacuated sample vacuum chamber. The sample vacuum chamber is maintained, before the start of the sequence, at a vacuum that is higher (closer to absolute vacuum) than the process vacuum chamber.

The gas sample in the sample vacuum chamber is then raised to atmospheric pressure after closing off the communication with the process vacuum chamber by adding a clean (particle-free) gas to the sample chamber. The gas sample, at atmospheric pressure, and still containing the particles from the process vacuum chamber sample, is then flushed out of the sample chamber into a particle measuring instrument. An optical particle counter or a condensation nucleus counter, both well known and conventional, but accurate instruments, can be used.

The pressure difference between the process vacuum chamber and the sample vacuum chamber, and the volume of the sample vacuum chamber are known, so the relationship between original particle concentration in the process vacuum chamber and the measured particle concentration in the sample taken and flushed through the sample vacuum chamber and counter can be calculated. This relationship can then be applied as a correction factor to convert the measured particle concentration in the sample chamber, after bringing the chamber up to atmospheric pressure, to the original particle concentration in the process vacuum chamber. The results can be expressed as the number of particles per unit volume in the process vacuum chamber, which is the critical parameter that must be measured to insure that particles will not contaminate the process.

Cycling of the valves in the steps of the process can be done automatically, by sequential controls on the valves utilizing conventional programming techniques. Timing of the various valve openings and closings can be arranged as desired to insure that an adequate gas sample is taken, and that it is handled without further contamination.

By providing a plurality of the sampling systems for one process vacuum chamber, substantially real time information can be provided on a continuous basis.

The sample vacuum chamber can be made according to known techniques, and standard valves, gas sources and absolute filters can be utilized in a unique sequence for providing the benefits of the present invention.

BRIEF DESCRIPTION OF THE DRAWINGS

FIG. 2 is a schematic timing diagram of valve sequencing used with the present invention.

DETAILED DESCRIPTION OF THE PREFERRED EMBODIMENTS

Figure 1:
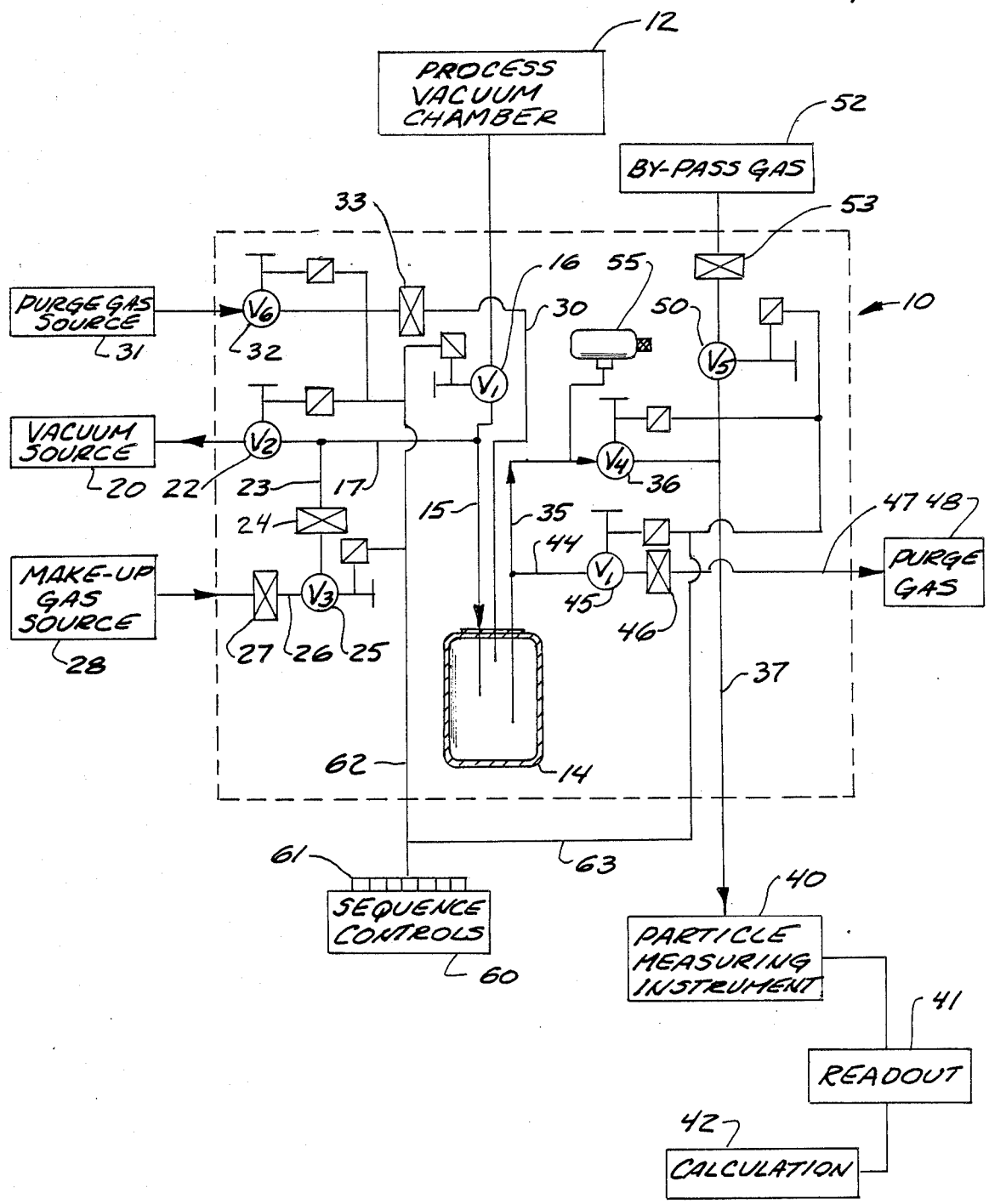
FIG. 1 is a schematic representation of an apparatus used for obtaining particle samplings in a vacuum, and made according to the present invention.

Referring to FIG. 1, a device made according to the present invention is illustrated schematically. The particle sampler or sampling system for vacuums indicated generally at 10 is made for sampling the aerosols in the gas of a process vacuum chamber 12, which can be used for processing semiconductor wafers or other materials. The process vacuum chamber has to have a clean, particle-free atmosphere in order to avoid having particles contaminate the parts being processed. The process vacuum chamber 12 is conventionally used in processing semiconductor wafers for various electronic components.

The process vacuum chamber 12 is maintained at a desired level of vacuum, but not at an extremely high vacuum level. The sampling arrangement 10 includes a sample vacuum chamber 14, which can be a stainless steel chamber of a suitable volume, so that the sample that is taken will be of adequate size for particle counting. The process vacuum chamber is connected to the sample vacuum chamber through a main line 15 and a control valve 16.

The sample vacuum chamber 14 is also connected to a very efficient vacuum pump or source 20, through a valve 22 connected into a line 17 that leads to main vacuum line 15 and then into the interior of the sample vacuum chamber 14. The valve 22 controls communication of the vacuum source 15 and the lines 17, and 15, which are in fluid communication with each other.

The valves 16 and 22 as well as the other valves in the present system are conventional air operated bellows valves that can be controlled by remote signals, or manually, and are illustrated schematically for automatic control.

The line 17 is also connected to a line 23 that has an absolute filter 24 therein. A third valve 25, again of the same type is on the input side of filter 24 and controls flow through a line 26 leading from a makeup gas source 28. An absolute filter 27 is in line 26 to filter gas from the makeup gas source 28. The makeup gas source 28 can be isolated from the sample vacuum chamber 14 by the use of valve 25. The makeup gas is filtered twice with absolute high efficiency filters 27 and 24 before the gas is admitted into sample vacuum chamber 14.

Additionally, a separate line 30 is open to the interior of the sample vacuum chamber 14, and line 30 leads from a purge gas source 31, through a valve 32 and an absolute filter 33 that will take out very, very fine particles, so that there are essentially no particles remaining in the gas from the source 31 when it is caused to flow into sample vacuum chamber 14.

Valve 32 is controllable to provide or close off communication between the purge gas source 31 and the sample vacuum chamber 14. A third line 35 leads from the sample vacuum chamber 14 and is connected through a valve 36 to a line 37 leading to a particle measuring instrument 40 of conventional design. The particle measuring instrument 40 will have a suitable readout 41 that can be instrumentation indicating the total number of particles that are in the gas sample passing through the particle measuring instrument. This readout can also provide electrical or other types of signals to a calculation computer 42. Suitable controls responsive to signals from the particle measuring instrument can be provided so that a correlation between the actual particles counted and the particles present in the process vacuum chamber can be provided by simple mathematical analysis.

Also, the particle measuring instrument can be calibrated by providing a known particle concentration in the process vacuum chamber, and carrying out a sampling sequence to determine, by analysis, needed calibration factors.

A line 35 is also connected through a line segment 44 and a valve 45, and through an absolute filter 46 to an output line 47 that is used for expelling purge gas from the sample vacuum chamber 14 into a purge gas reservior 48.

A valve 50 is located in the line 37 and controls flow from a bypass gas source 52 through an absolute filter 53 to the particle measuring instrument 40. This bypass gas is used during the time when the sample vacuum chamber 14 is being purged and filled, and before the contents of the sample vacuum chamber are passed through the particle measuring instrument 40.

A vacuum gauge 55 can be utilized in the line 35 for determining the vacuum level in the sample vacuum chamber when valve 36 is closed.

A sequence control programmer indicated generally at 60 has a number of output lines 61 that are combined into cables, as shown at 62 and 63 with the individual lines used to control the respective valves 16, 22, 25, 32, 36, 45 and 50.

The operation for a complete cycle of measuring particles from the process vacuum chamber involves sequentially operating the various valves. All of the valves, namely valves 16, 22, 25, 32, 36, 45 and 50 are normally closed when the cycle starts. Valves 32 and 45 are opened, and when valve 32 is open purge gas will flow through the absolute filter 33, through line 50, and into the sample vacuum chamber 14, and purges the atmosphere in the chamber 14 out through line 35, and line 44, through valve 45 and filter 46 and thus out through line 47 to the purge gas reservoir 48. The purge gas will flush through the sample vacuum chamber 14 to insure that the chamber 14 is free of all particulate contaminants before the start of a measurement cycle. Valves 32 and 45 are used for the initial purging and are not used for the subsequent measurement cycle.

The high efficiency or absolute gas filters provided in the flow passage for the purge gas insures that the purge gas is clean and has no suspended aerosol particles. The absolute or high efficiency gas filter 33, as well as the filter 46, are known filters that are capable of removing particles from the purge gas.

With the process vacuum chamber 12 under a suitable vacuum, and the purging of sample vacuum chamber 14 completed, all the valves are closed including valve 16 in line 15, which is the main sampling line. The sample vacuum chamber 14 is then reduced in pressure by connecting the chamber to a vacuum source 20 through the valve 22, which is opened in sequence in response to a suitable control signal. This will provide a vacuum to the chamber 14 which is at a higher vacuum than the vacuum in the process vacuum chamber 12. Valve 22 will remain open for a sufficiently long period of time so that sampling chamber 14 attains a very high vacuum level, typically a few millitorrs, and sometimes as high as a few microtorrs, corresponding to the lowest pressure produced by the vacuum pump or source 20. Once the vacuum has stabilized so that the sample vacuum chamber 14 is at the low level desired, valve 22 is closed and valve 16 is opened to allow the aerosol sample, that is, the gas from the process vacuum chamber 12 and the particles contained therein, to flow into the sample vacuum chamber 14. The sample transfer occurs because the sample vacuum chamber 14 is at a lower pressure than the process vacuum chamber or equipment before valve 16 is opened.

A few moments are allowed so that the pressure levels in the sample vacuum chamber 14 and the process vacuum chamber 12 equalize, and then the valve 16 is closed so that the sample of gas in the sample vacuum chamber 14 is the same constituency as that in the process vacuum chamber 12. The sample vacuum chamber, which is isolated from the process vacuum chamber 12, and the pressure in sample vacuum chamber 14, is brought up to atmospheric pressure by opening the valve 25 which connects the makeup gas source 28 through lines 26 and 23, as well as line 15 to the sample vacuum chamber 14. The makeup gas source 28 raises the pressure in sample vacuum chamber 14 to atmospheric.

The makeup gas source is a clean, dry gas such as dry nitrogen, and it is introduced to sample vacuum chamber 14 through two absolute or high efficiency gas filters 27 and 24 to insure that no particles are present. The makeup gas source is therefore completely or substantially particle-free.

Once the sample vacuum chamber 14 is at atmospheric pressure, the aerosols in the sample vacuum chamber are counted. It should be noted that valve 25 is left open, and the valve 36 is also opened by a suitable control. When valve 36 opens, as controlled by the sequence control 60, the line 35 is connected to the line 37 leading to the particle measuring instrument 40. Valve 50 is closed before valve 36 is opened, so there is then a flow of gas at atmospheric pressure from source 28, through filter 27, valve 25, filter 24, and lines 23, 17 and 15, into the interior of the sample vacuum chamber 14 and then back out through line 35, valve 36 and line 37 to the particle measuring instrument 40. The aerosol sample is flushed out of the sample vacuum chamber by the makeup gas flow and is flushed through the particle measuring instrument 40. The aerosol particles in the gas sample being flushed out of the sample vacuum chamber are then measured by the particle measuring instrument 40, which provides a suitable readout 41, from which calculations can be made.

After the sample that had been taken from the process vacuum chamber 12 is completely flushed out of the sample vacuum chamber 14, and the particle measuring instrument 40 indicates no further particles are being counted, the valves 25 and 36 are closed. To avoid having to stop the particle measuring instrument while no particles are being measured, the valve 50 is opened in sequence to allow a steady stream of particle-free gas to flow from the bypass gas source 52, through an absolute or high efficiency filter 53, valve 50 and line 37 into the particle measuring instrument to keep the instrument operating. The instrument thus will be standing in a ready state for the next sample to be introduced into the instrument for analysis.

In a test apparatus, a sample vacuum chamber volume of about 250 $cm^3$ was used, and it was found that the evacuation time of the sample vacuum chamber of about 10 seconds was satisfactory. Faster pumping resulted in a rapid temperature drop in the sample vacuum chamber and caused substantial background counts of particles, due to condensation leading to the production of ultrafine aerosols. The measurement of the actual aerosol sample from the process vacuum chamber 12 is the most time consuming process and can take from 45 seconds to 120 seconds, depending on particle concentration. Process chamber sampling and pressure equalization between the process vacuum chamber and the sample vacuum chamber typically is done within about five seconds. Times can vary, depending on the size of and the level of vacuum in the sample vacuum chamber 14.

One effect that has to be taken into account is the loss of aerosol particles in the short time period the sample is in the sample vacuum chamber 14. This loss of particles can be due to particles settling on the bottom of the chamber by gravity, and also can be due to diffusion of particles into the walls of the sample vacuum chamber. These losses can be calculated theoretically, as exemplified in the Crump et al. article mentioned in the Background of the Invention. Since the dwell time in the sample vacuum chamber is quite low, the loss does not seem to be very important for particles in the range of 0.1 to 1.0 micron range, and for particles outside that range, corrections can be made to account for particle loss in the sample vacuum chamber. The loss of particles during their passage from the process vacuum chamber 12 into the sample vacuum chamber 14 also must be taken into account. There are some losses from the sample in the particles measuring instrument 40, and the determination of such losses can be calibrated for each individual system before the system is used for actual measurement.

The efficiency of the present device has been demonstrated experimentally by introducing particles into a vacuum chamber, such as process vacuum chamber 12, and then sampling the atmosphere with the system described above. The measured size distribution of the aerosols in the vacuum chamber, comprising process vacuum chamber 12, was found to be the same as that of the original aerosol introduced into the vacuum chamber. Such experiments show that the system is feasible and adequate for measurement of particles in a vacuum.

It should be noted that other tests have shown that pumping down the sample vacuum chamber 14 faster than a desired speed results in the generation of a larger number of particles than a slower pumping speed, which is attributed to particle generation in the system itself.

The sequence or method of operation can be placed into a table form utilizing the operating valves for the actual process. The table is for operation after the purging of the sample vacuum chamber 14 to clear it of any unwanted contaminants. Table 1 below sets forth this sequence:

TABLE 1

| Measurement Step | V16 | V22 | V25 | V36 | V50 |
| --- | --- | --- | --- | --- | --- |
| Evacuation of sampling chamber to a preset pressure | C | O | C | C | O |
| Sampling from the vacuum equipment into the sampling chamber | O | C | C | C | O |
| Pressure equalization in the sampling chamber using makeup gas | C | C | O | C | O |
| Sample measurement at atmospheric pressure from the sampling chamber | C | C | O | O | C |

(C means closed; O means open.)

The above steps permit use of existing equipment for measuring particles, down to 0.01 microns in size directly from a vacuum chamber, so that the conditions in a process vacuum chamber can be accurately monitored in insure repeatability of the process and avoid loss of yield due to particle contamination. A condensation nucleus counter is used as the particle measuring instrument 40. The present method and apparatus for the first time permits small particles in a vacuum to be measured directly. FIG. 2 illustrates the timing of the valves through one cycle. The valves 16, 22, 25, 36 and 50 are each represented by a plot line with time (t) increasing toward the right. The representation of the timing shows the valve operational sequence.

Although the present invention has been described with reference to preferred embodiments, workers skilled in the art will recognize that changes may be made in form and detail without departing from the spirit and scope of the invention.

What is claimed is:

1. A particle measuring apparatus for sampling a gas in a first chamber having a vacuum level comprising:
    a sample vacuum chamber that is maintained at a vacuum lower than that of the vacuum in the first chamber;
    first valve means for controlling gas flow from the first chamber into the sample vacuum chamber when the first valve means is open;
    second valve means for providing gas into the sample vacuum chamber subsequent to closing of the first valve means, and operable to provide as gas flow through the sample vacuum chamber; and
    particle measuring means connected to the sample vacuum chamber and controlled to receive gas from the sample vacuum chamber when the flow through the second valve means is occurring, whereby the gas in the sample vacuum chamber is purged through the sample vacuum chamber and into the particle measuring means.

2. The apparatus as specified in claim 1 and third valve means connected to control flow from said sample vacuum chamber to the particle measuring means independently of flow through the second valve means.

3. The apparatus as specified in claim 2 wherein the second valve means is connected to a makeup gas source, and high efficiency filter means between the makeup gas source and the sample vacuum chamber for filtering particles from the gas from the makeup gas source when the second valve means is open.

4. The apparatus as specified in claim 3 and a separate vacuum pump means, and fourth valve means for opening the separate vacuum pump means to said sample vacuum chamber to permit creating a vacuum in said sample vacuum chamber that is higher than that of the first chamber system.

5. The apparatus as specified in claim 1 wherein said first chamber comprises a process vacuum chamber for carrying out an industrial process.

6. The combination as specified in claim 5 and means for providing a purge gas flow through said sample vacuum chamber prior to creating a vacuum in said sample vacuum chamber, said means for providing a purge gas flow including filter means for filtering particles from the purge gas.

7. A method of counting particles in a gas in a vacuum system comprising the steps of:
    removing a sample of gas and particles from the vacuum system to a separate sample vacuum chamber;
    fluidly isolating the vacuum system from the sample vacuum chamber;
    providing a flow through said sample vacuum chamber to expel the particles from the sample obtained from the vacuum system out of the sample vacuum chamber; and
    counting particles expelled from the sample vacuum chamber.

8. The method of claim 7 including the step of equalizing the pressure in the sample vacuum chamber to substantially atmospheric pressure prior to providing a flow out of the sample vacuum chamber for counting of particles.

9. The method of claim 7 including the step of evacuating the sample vacuum chamber to a vacuum level higher than that of the vacuum system, and then opening a valve to provide flow from the vacuum system to the sample vacuum chamber to provide the sample of aerosols in the sample vacuum chamber.

10. The method of claim 7 including the step of purging particles and atmosphere from the sample vacuum chamber prior to creating a vacuum in the sample vacuum chamber.

11. A particle measuring apparatus for sampling a gas in a first chamber having a vacuum level comprising:
    a sample vacuum chamber that is maintained at a vacuum lower than that of the vacuum in the first chamber;
    means for selectively controlling gas flow from the first chamber into the sample vacuum chamber to provide a sample of gas from the first chamber in the sample chamber;
    means for providing a gas flow through the sample vacuum chamber after a sample of gas from the first chamber is in the sample vacuum chamber; and
    particle measuring means connected to the sample vacuum chamber and controlled to receive gas from the sample vacuum chamber when the gas flow through the sample vacuum chamber is occurring, whereby the gas from the first chamber which is in the sample vacuum chamber is purged into the particle measuring means.

* * * * *

UNITED STATES PATENT AND TRADEMARK OFFICE
CERTIFICATE OF CORRECTION

PATENT NO. : 4,928,537
DATED : May 29, 1990
INVENTOR(S) : Benjamin Y. H. Liu et al.

It is certified that error appears in the above-identified patent and that said Letters Patent is hereby corrected as shown below:

Col. 7, line 58, delete "as", insert --a--.

Signed and Sealed this

Fifteenth Day of October, 1991

*Attest:*

HARRY F. MANBECK, JR.

*Attesting Officer*   *Commissioner of Patents and Trademarks*